United States Patent [19]
Echeverry et al.

[11] Patent Number: 6,015,421
[45] Date of Patent: *Jan. 18, 2000

[54] APPARATUS AND METHOD FOR DEVELOPING AN ANATOMIC SPACE FOR LAPAROSCOPIC PROCEDURES

[75] Inventors: Jan M. Echeverry, San Jose; Luis M. Fernandez, Palo Alto; James E. Jervis, Atherton; Janine C. Robinson, Half Moon Bay; Shigeru Tanaka, Palo Alto; Laveille K. Voss, Belmont, all of Calif.

[73] Assignee: General Surgical Innovations, Inc., Cupertino, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/857,193

[22] Filed: May 15, 1997

[51] Int. Cl.⁷ ................................................. A61M 29/00
[52] U.S. Cl. ......................... 606/190; 606/192; 604/96
[58] Field of Search .................................. 606/190, 191, 606/194, 192; 600/207; 604/96–101

[56] References Cited

U.S. PATENT DOCUMENTS

| | | |
|---|---|---|
| Re. 29,207 | 5/1977 | Boldac et al. . |
| 512,456 | 9/1894 | Sadilkova . |
| 1,213,005 | 1/1917 | Pillsbury . |
| 2,936,760 | 5/1960 | Gants . |
| 3,545,443 | 12/1970 | Ansari et al. . |
| 3,774,596 | 11/1973 | Cook . |
| 3,800,788 | 4/1974 | White . |
| 3,882,852 | 5/1975 | Sinnreich . |
| 4,083,369 | 4/1978 | Sinnreich . |
| 4,217,889 | 8/1980 | Radovan et al. . |
| 4,243,050 | 1/1981 | Littleford . |
| 4,276,874 | 7/1981 | Wolvek et al. . |
| 4,312,353 | 1/1982 | Shahbabian . |
| 4,411,654 | 10/1983 | Boarini et al. . |
| 4,490,137 | 12/1984 | Moukheibir . |
| 4,496,345 | 1/1985 | Hasson . |
| 4,574,806 | 3/1986 | McCarthy . |
| 4,581,025 | 4/1986 | Timmermans . |
| 4,596,554 | 6/1986 | Dastgeer . |
| 4,644,936 | 2/1987 | Schiff . |
| 4,654,030 | 3/1987 | Moll et al. . |
| 4,685,447 | 8/1987 | Iversen et al. . |
| 4,738,666 | 4/1988 | Fuqua . |
| 4,769,038 | 9/1988 | Bendavid et al. . |
| 4,772,266 | 9/1988 | Groshong . |
| 4,779,611 | 10/1988 | Grooters et al. . |
| 4,784,133 | 11/1988 | Mackin . |
| 4,793,348 | 12/1988 | Palmaz . |

(List continued on next page.)

FOREIGN PATENT DOCUMENTS

| | | |
|---|---|---|
| 92 107 498 | 5/1992 | European Pat. Off. . |
| 0 573 273 A2 | 6/1993 | European Pat. Off. . |
| WO 92/06638 | 4/1992 | WIPO . |

*Primary Examiner*—Michael Buiz
*Assistant Examiner*—William W. Lewis
*Attorney, Agent, or Firm*—Lyon & Lyon LLP

[57] ABSTRACT

An improved laparoscopic apparatus for tunneling to a desired anatomical location and developing a surgical space is disclosed, including a tunneling member adapted to receive a laparoscope therein and an inflatable balloon secured on the tunneling member. The tunneling member has a passage extending between its open proximal and distal ends. A lip is integrally formed on the distal end to retain a laparoscope inserted into the passage, the lip having a substantially rounded and blunt distal edge. The lip defines a recessed or open center area in the distal opening, enhancing the field of view of the laparoscope therethrough. The balloon is formed from flexible, transparent material, and is rolled and secured to the tunneling member. The balloon includes inverted seams and/or unfused outer edges adapted to minimize tissue trauma during inflation, and has an extended distal portion adapted to be unrolled during space development, thereby improving distal space development and enhancing visualization of landmarks within the space being developed.

30 Claims, 5 Drawing Sheets

U.S. PATENT DOCUMENTS

| | | |
|---|---|---|
| 4,798,205 | 1/1989 | Bonomo et al. . |
| 4,800,901 | 1/1989 | Rosenberg . |
| 4,802,479 | 2/1989 | Haber et al. . |
| 4,813,429 | 3/1989 | Eshel et al. . |
| 4,854,316 | 8/1989 | Davis . |
| 4,869,717 | 9/1989 | Adair . |
| 4,888,000 | 12/1989 | McQuilkin et al. . |
| 4,917,668 | 4/1990 | Haindl . |
| 4,931,042 | 6/1990 | Holmes et al. . |
| 4,955,895 | 9/1990 | Sugiyama et al. . |
| 5,002,557 | 3/1991 | Hasson . |
| 5,009,643 | 4/1991 | Reich et al. . |
| 5,030,206 | 7/1991 | Lander . |
| 5,030,227 | 7/1991 | Rosenbluth et al. . |
| 5,074,871 | 12/1991 | Groshong . |
| 5,104,383 | 4/1992 | Shichman . |
| 5,116,318 | 5/1992 | Hillstead . |
| 5,116,357 | 5/1992 | Eberbach . |
| 5,122,155 | 6/1992 | Eberbach . |
| 5,137,512 | 8/1992 | Burns et al. . |
| 5,141,494 | 8/1992 | Danforth et al. . |
| 5,141,515 | 8/1992 | Eberbach . |
| 5,147,302 | 9/1992 | Euteneuer et al. . |
| 5,147,374 | 9/1992 | Fernandez . |
| 5,158,545 | 10/1992 | Trudell et al. . |
| 5,159,925 | 11/1992 | Neuwirth et al. . |
| 5,163,949 | 11/1992 | Bonutti . |
| 5,176,692 | 1/1993 | Wilk et al. . |
| 5,183,463 | 2/1993 | Debbas . |
| 5,188,596 | 2/1993 | Condon et al. . |
| 5,188,630 | 2/1993 | Christoudias . |
| 5,195,507 | 3/1993 | Bilweis . |
| 5,201,742 | 4/1993 | Hasson . |
| 5,201,754 | 4/1993 | Crittenden et al. . |
| 5,209,725 | 5/1993 | Roth . |
| 5,215,526 | 6/1993 | Deniega et al. . |
| 5,222,970 | 6/1993 | Reeves . |
| 5,226,890 | 7/1993 | Ianniruberto et al. . |
| 5,232,446 | 8/1993 | Arney . |
| 5,258,026 | 11/1993 | Johnson et al. . |
| 5,269,753 | 12/1993 | Wilk . |
| 5,308,327 | 5/1994 | Heaven et al. . |
| 5,309,896 | 5/1994 | Moll et al. . |
| 5,314,443 | 5/1994 | Rudnick . |
| 5,318,012 | 6/1994 | Wilk . |
| 5,342,307 | 8/1994 | Euteneuer et al. . |
| 5,346,504 | 9/1994 | Ortiz et al. . |
| 5,359,995 | 11/1994 | Sewell, Jr. . |
| 5,361,752 | 11/1994 | Moll et al. . |
| 5,370,134 | 12/1994 | Chin et al. . |
| 5,383,889 | 1/1995 | Warner et al. . |
| 5,391,178 | 2/1995 | Yaper . |
| 5,402,772 | 4/1995 | Moll et al. . |
| 5,407,433 | 4/1995 | Loomas . |
| 5,425,357 | 6/1995 | Moll et al. . |
| 5,431,173 | 7/1995 | Chin et al. . |
| 5,468,248 | 11/1995 | Chin et al. . |
| 5,540,711 | 7/1996 | Kieturakis et al. . |
| 5,607,443 | 3/1997 | Kieturakis et al. .............. 606/192 |
| 5,772,680 | 6/1998 | Kieturakis et al. . |

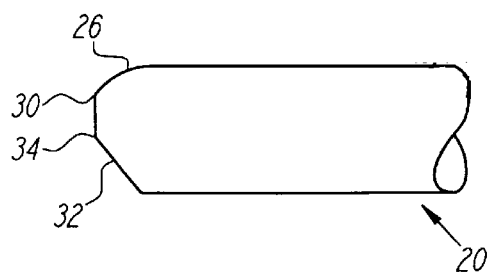
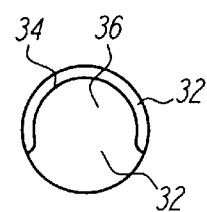
FIG. 2A    FIG. 2B
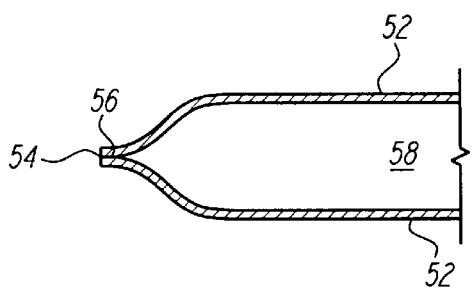
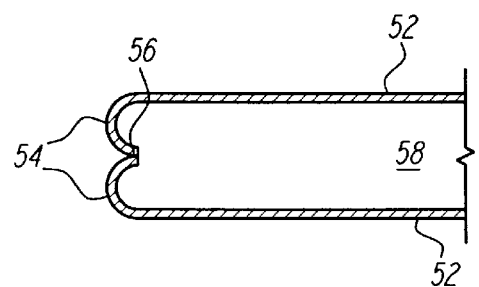
FIG. 3A    FIG. 3B
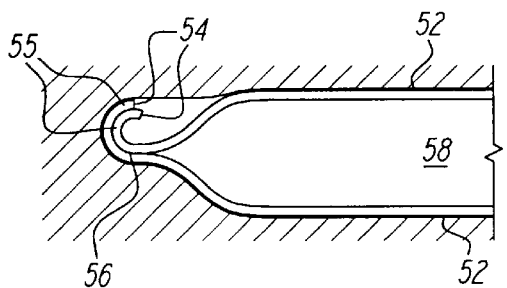
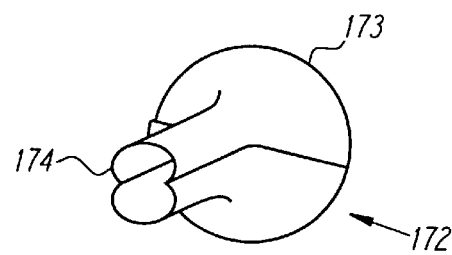
FIG. 3D    FIG. 3C
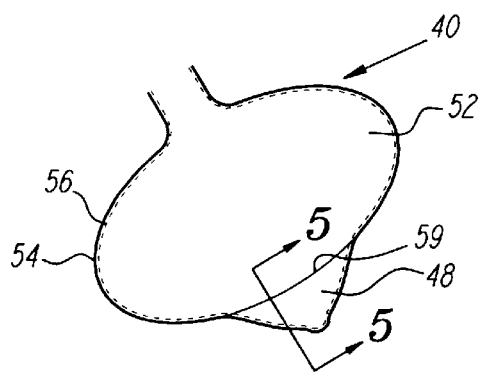
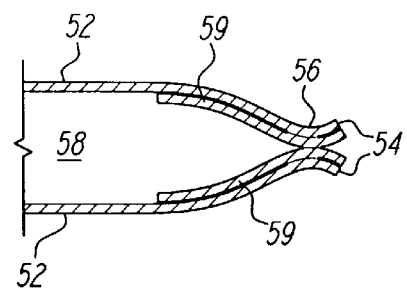
FIG. 4    FIG. 5

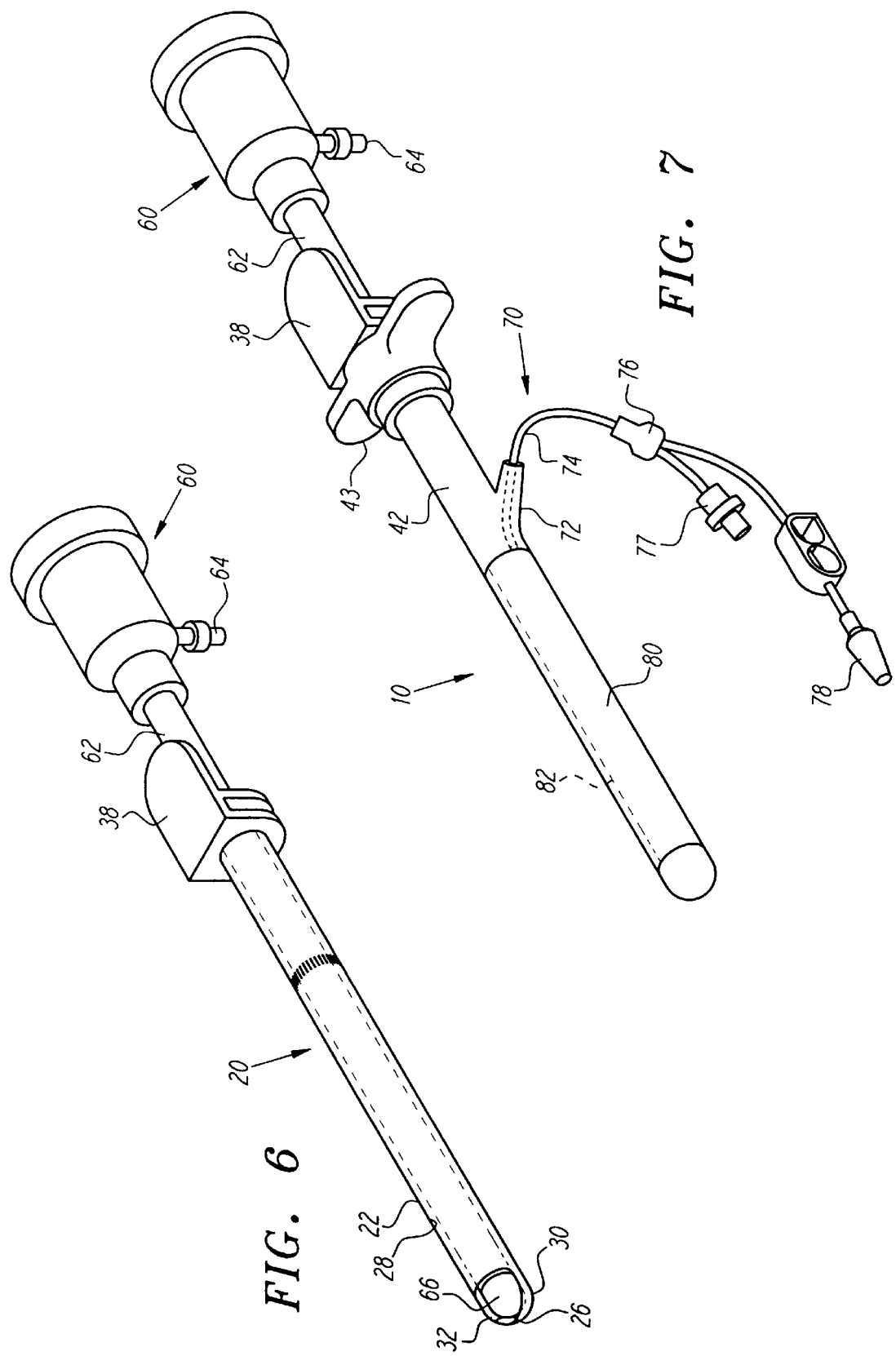

APPARATUS AND METHOD FOR DEVELOPING AN ANATOMIC SPACE FOR LAPAROSCOPIC PROCEDURES

FIELD OF THE INVENTION

The present invention relates generally to an apparatus and method for developing an anatomic space for laparoscopic procedures, and more particularly to an apparatus and method for providing laparoscopic visualization during tunneling to a desired anatomic space as well as during subsequent balloon inflation to develop the desired space.

BACKGROUND

A number of surgical devices may be used to develop a surgical space within a body. For example, blunt dissectors or soft-tipped dissectors may be utilized to create a dissected space which is parallel to the plane in which the dissectors are introduced into the body.

More recently, surgical devices including an inflatable balloon have been used to develop an anatomic space. Such devices typically include an elongate shaft or obturator for tunneling into the body with the balloon attached to it. The balloon is generally collapsed initially, for example by gathering the balloon about the shaft, and is secured to the shaft by a tubular sheath or cover. The tunneling shaft with the deflated balloon thereon is introduced into the body and directed to a desired location. Once the desired location is reached, the balloon is deployed by inflation to develop the anatomic space, generally causing dissection along a natural plane within the tissue structures.

The balloon generally comprises two similarly shaped panels that are heat sealed, sonic welded or otherwise substantially fused together along their outer edges, creating a substantially fluid tight seam around the balloon. Although the material comprising the balloon panels is generally flexible, the material may become stiff and/or abrasive along the seam. During tunneling or when the balloon is deployed, an external seam may move along the tissues in the anatomic space being developed, potentially causing tissue trauma, particularly in sensitive tissues, and/or resulting in undesired bleeding in the space.

More particularly, in relation to laparoscopic procedures, surgical devices have been developed that permit visualization during tunneling as well as during development of the anatomic space. Such devices typically include a tunneling shaft, an inflatable balloon, and a laparoscope. The tunneling shaft comprises a substantially rigid tubular member having open proximal and distal ends, defining a passage adapted to receive a laparoscope therein. The balloon is generally formed from substantially transparent material, thereby allowing observation through the balloon wall. The distal end of the tunneling shaft may be inserted through a proximal end of the balloon into the interior of the balloon. Similar to other tunneling devices, the balloon is initially collapsed around the tunneling shaft and may be covered by a sheath.

The distal end of the tunneling shaft generally includes a lip partially obstructing the open distal end. The lip may be formed by providing a rounded tip on the distal end of the shaft and cutting away an angled section of the tip, for example at a forty five degree angle. The lip prevents a laparoscope inserted into the tunneling shaft from extending beyond the distal end of the shaft.

During tunneling, a laparoscope inserted into the tunneling shaft may be positioned for focus and used to observe the progress of the device, the transparent balloon wall allowing observation through the open distal end of the tunneling shaft. Once the desired location is reached, the balloon is inflated. During inflation, the distal end of the tunneling shaft and laparoscope may be moved around within the balloon to view the space being developed, to observe tissue dissection, and to identify tissue structures.

One problem with such devices is that the lip on the tunneling shaft may result in a sharp distal edge. This sharp edge may contribute to tissue trauma when the tunneling shaft is introduced into a body, and/or when the tunneling shaft is moved to observe the anatomic space being developed. The sharp edge may also damage or puncture the balloon, possibly requiring removal and replacement of the device.

In addition, the lip may substantially obstruct the field of view of the laparoscope. Although the tunneling shaft often comprises substantially transparent material in order to transmit light, distortion through the walls may impair peripheral visualization. Thus, the most effective field of view through the laparoscope is generally through the open distal end of the tunneling shaft. Because the lip partially blocks the distal end, however, the lip often obstructs the axial field of view. For this reason, such devices often employ an angled rather than a straight laparoscope, providing visualization at an angle out the open distal end, rather than in an axial direction. Thus, to fully view the tissues being dissected, the tunneling shaft may have to be rotated axially, which may be disfavored in some procedures.

Accordingly, there is a need for an apparatus and method for developing an anatomic space which provides improved visualization during tunneling and subsequent space development.

In addition, there is a need for a laparoscopic apparatus and method for developing an anatomic space which substantially minimizes tissue trauma during tunneling and development of the space, thereby reducing bleeding that may obscure the field.

SUMMARY OF THE INVENTION

The present invention is directed to an apparatus and method for observing tissue dissection while tunneling to a desired location within a body and for developing an anatomic space at the desired location. Generally, the apparatus includes a tunneling member and an inflatable balloon. The tunneling member comprises a substantially rigid tubular shaft having proximal and distal ends, having a passage extending between the ends, and having an opening in the proximal end to receive a conventional laparoscope. The proximal end of the shaft may include a handle thereon for directing the shaft during a procedure.

The distal end is generally truncated and includes an integrally formed lip. Preferably, the lip has a substantially rounded, blunt distal edge, adapted to minimize tissue trauma. In addition, the lip preferably is "U" shaped, partially defining an opening adjacent the axis of the shaft having a recessed center in the opening, to enhance visualization and minimize obstruction of the field of view through the distal end.

The balloon generally comprises a substantially flexible, and preferably non-elastomeric, material having an inflatable space therein, defining a predetermined shape capable of assuming collapsed and inflated conditions. Preferably, the balloon has a substantially circular or elliptical shape, except for a bulge or extension in a distal portion of the balloon.

The balloon generally comprises two panels of material that are fused or welded together around their periphery, creating a substantially fluid tight seam that defines the inflatable space of the balloon and provides substantially flexible outer edges for the balloon. Preferably, flexible outer edges are provided by fusing or welding the panels on their periphery, such as by heat sealing or sonic welding, to create a seam, turning the panels inside out, thereby creating an inverted seam which extends slightly into the inflatable space in the balloon and a reentrant outer profile at the seam on the balloon. Alternatively, the seam may be welded and set in by a predetermined margin from the outer edges of the panels. The balloon may also be selectively strengthened, by attaching or welding reinforcing panels to the walls of the balloon, such as in the distal portion of the balloon.

The balloon generally includes a proximal sleeve or neck having a sealable opening therein, preferably having a handle with a bore therethrough that communicates with the inflatable space within the balloon. The distal end of the tunneling member may be directed into the inflatable space of the balloon through the bore in the handle, seals in the handle providing a substantially fluid tight seal. Alternatively, the neck may be sealably attached directly to the outer wall of the tunneling member or the handle.

Prior to use, the tunneling member and balloon are generally assembled, and a conventional laparoscope or similar device is usually provided. Preferably, the balloon includes a bulge or extension in its distal portion, and the distal end of the tunneling member is inserted until it reaches, but does not enter, the distal portion of the balloon. Optionally, the distal end of the balloon may be reinforced by thicker or multiple sheets of balloon material suitably welded thereto.

The balloon is rolled, gathered or folded about the shaft of the tunneling member, or is provided pre-rolled, preferably as follows. The bulge in the distal portion of the balloon is first rolled proximally onto the anterior or top surface of the balloon. The sides of the balloon are then rolled laterally inward onto the posterior or bottom surface of the balloon, until the balloon is substantially collapsed around the shaft of the tunneling member. Alternatively, if the distal end of the tunneling member is directed to the outer edge of the distal portion of the balloon, the distal portion may not be rolled proximally before the sides are rolled laterally in. The balloon is then secured, preferably by a removable sheath or integral cover that substantially holds the balloon until the balloon is ready to be deployed. U.S. Pat. No. 5,540,711, the disclosure of which is incorporated herein by reference, describes sheaths and covers that may be used for embodiments of a balloon in accordance with the present invention.

A laparoscope is generally inserted into the proximal end of the tunneling member, preferably until it engages the lip on the distal end of the shaft. The apparatus is then ready to be introduced into a body, for example between layers of the abdominal wall to create a preperitoneal space for laparoscopic hernia repair. For such a procedure, an incision is made in the skin of a patient to access the desired tissue layer, and the distal end of the tunneling member, together with the laparoscope and rolled balloon, is introduced into the incision. The tunneling member is advanced through the body tissue to the desired location. Although the balloon covers the opening in the distal end of the tunneling member, the substantially transparent material of the balloon allows some observation of tissue during advancement of the tunneling member using the laparoscope.

Once the tunneling member reaches the desired location, the balloon is deployed by removing the sheath or cover, thereby exposing the balloon. The balloon is then inflated by introducing fluid, such as saline solution, through an inflation lumen into the inflatable space in the balloon (if an integral sheath is used to contain the balloon, inflation will burst the sheath). This causes the balloon to expand, unrolling the rolled portions, causing tissue dissection and developing the anatomic space.

The method of preparing the collapsed balloon described above is particularly useful in developing a preperitoneal space for laparoscopic hernia repair. Prior to balloon inflation, the tunneling member is preferably oriented such that the anterior surface of the balloon is directed towards the posterior side of the pubis. As the balloon is inflated, the side portions unroll first, thereby substantially anchoring the balloon. The distal portion then unrolls, extending the anatomic space distally, allowing improved space development and exposure of anatomic landmarks.

In addition, as the distal portion unrolls, it engages the posterior surface of the pubis, abrading the surface to clear the field and enhance observation, particularly of Cooper's ligament. Cooper's ligament is a useful body structure for orienting the surgeon within the preperitoneal space. Cooper's ligament has a substantially white appearance and may be more easily observed when free of other tissues, thus providing an important landmark within the space.

An additional feature of the apparatus of the present invention is the improved seam of the balloon provided. During balloon inflation as the side portions and distal portion of the balloon unroll, the peripheral edges engage and move along tissues within the space. A balloon in accordance with the present invention may have substantially less or no outwardly protruding seam edges which might contribute to tissue trauma or bleeding and obstruction of the surgical field.

Accordingly, a principal object of the present invention is to provide an improved apparatus and method for developing an anatomic space within a body that provides improved visualization and/or substantially minimizes tissue trauma during tunneling and subsequent space development.

Other objects and features of the present invention will become apparent from consideration of the following description taken in conjunction with the accompanying drawings.

BRIEF DESCRIPTION OF THE DRAWING

FIG. 2A is a plan view of a distal end of a tunneling member for a laparoscopic apparatus in accordance with the present invention.

FIG. 2B is an end view of the distal end of the tunneling member shown in FIG. 2A.

FIG. 3A is a cross-sectional view taken along line 3—3 of FIG. 1, showing an external seam of the balloon prior to inverting the balloon.

FIG. 3B is a cross-sectional view taken along line 3—3 of FIG. 1, showing a preferred embodiment of the inverted seam of the balloon in accordance with the present invention after inverting the balloon.

FIG. 3C is a perspective view of an adapter nipple for attaching an inflation lumen to a balloon in accordance with the present invention.

FIG. 3D is a cross-sectional view of an alternative embodiment of the peripheral seam of the balloon, with the outer edges engaging a tissue surface.

FIG. 4 is a perspective view of a balloon for a laparoscopic apparatus in accordance with the present invention having reinforcing panels attached thereto.

FIG. 5 is a cross-sectional view taken along line 5—5 of FIG. 4, showing the reinforcing panels attached to the balloon.

FIG. 6 is a perspective view of a tunneling member with a laparoscope inserted therein for a laparoscopic apparatus in accordance with the present invention.

FIG. 7 is a perspective view of a laparoscopic apparatus in accordance with the present invention, showing the balloon covered by a removable sheath and having a laparoscope inserted into the assembled tunneling member.

DETAILED DESCRIPTION OF THE PREFERRED EMBODIMENTS

Figure 1:
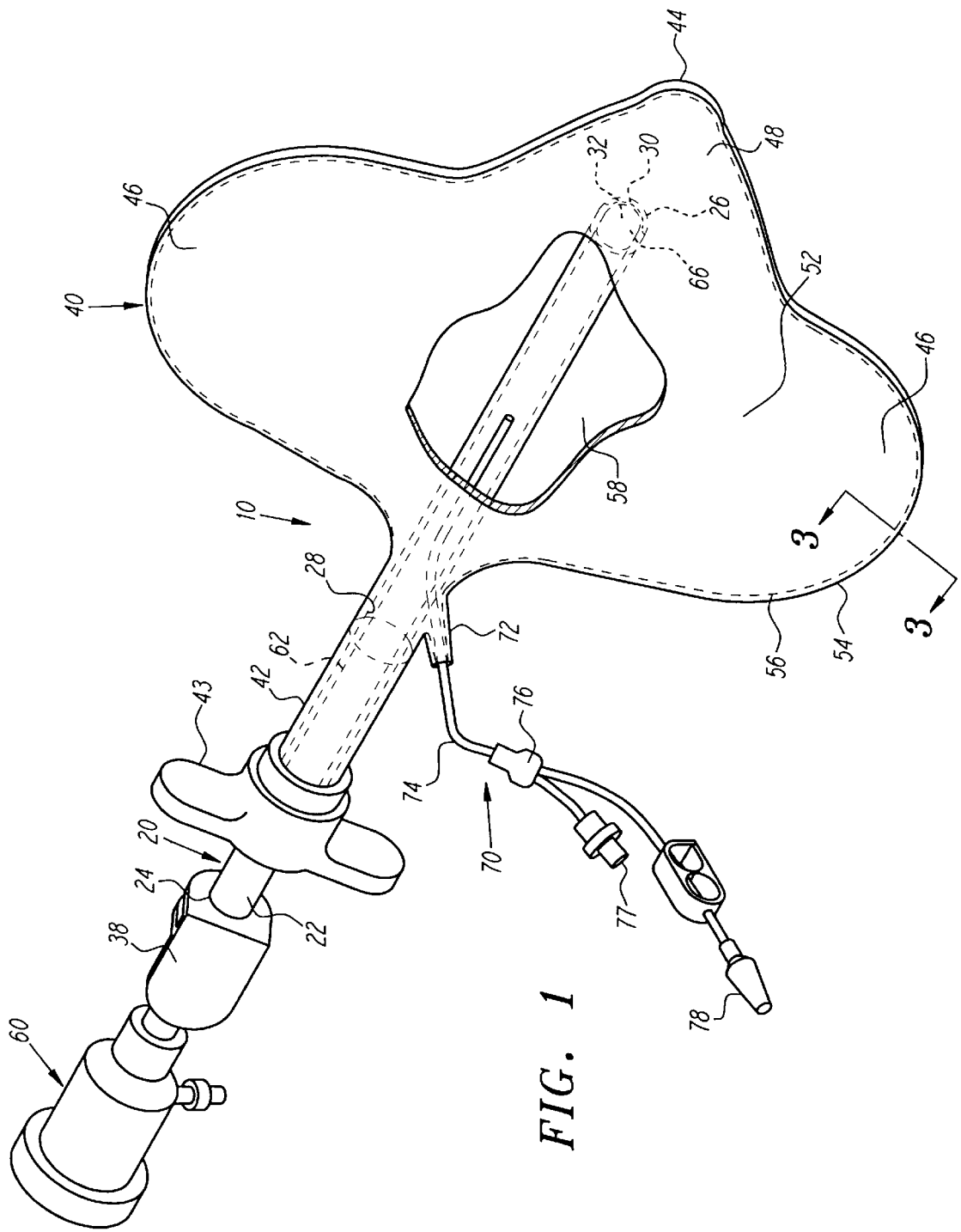
FIG. 1 is a perspective view of a preferred embodiment of a laparoscopic apparatus in accordance with the present invention, with the balloon uncovered and unrolled.

Turning to the drawings, FIG. 1 shows a preferred embodiment of a laparoscopic apparatus 10 in accordance with the present invention. The apparatus 10 includes a tunneling member 20, and an inflatable balloon 40. The tunneling member 20, which may be formed from a suitable medical grade plastic, such as polycarbonate, comprises an obturator shaft 22 and a handle 38. The obturator shaft 22 is sufficiently rigid to permit tunneling through tissue layers within the human body. The shaft 22 has an open proximal end 24, an open distal end 26, and a passage 283 extending between the proximal end 24 and the distal end 26 adapted to receive a conventional laparoscope 60 therein. The handle 38 is attached to the proximal end 24 of the shaft 22, thereby allowing a surgeon to grasp and manipulate the shaft 20 during performance of a procedure. The handle 38 preferably includes a bore (not shown) therethrough that communicates with the passage 28 in the shaft 20, and includes fluid seals (not shown) therein allowing the laparoscope 60 to be sealably inserted into the passage 28 and allowing balloon inflation.

The distal end 26 includes an integrally formed retaining lip 30 for containing the laparoscope 60 inserted into the tunneling member 20, and preventing the laparoscope 60 from extending beyond the distal end 26. Generally, the lip 30 has a substantially rounded, blunt distal edge 34, as shown in FIGS. 2A and 2B. Preferably, the lip 30 extends radially inward from the perimeter of the tunneling member 20 around the distal end 26, thereby defining a substantially "U" shaped distal edge 34. The distal edge 34 of the lip 30 defines a recessed or open center area 36 in the opening 32, thereby substantially minimizing obstruction of the opening 32, and enhancing the field of view axially through the distal end 24, as explained below.

Referring once again to FIG. 1, the balloon 40 generally comprises a substantially round or elliptical shaped body having an inflatable space 58 therein, and including side portions 46 and a bulge or extension in a distal portion 48 of the balloon 40. The balloon 40 is generally formed from substantially flexible sheet material, preferably a suitable non-elastomeric medical-grade material such as polyvinyl chloride or polyurethane. The balloon 40 thus preferably defines a predetermined shape capable of assuming collapsed and inflated conditions. In addition, the material is preferably substantially transparent, thereby allowing visualization through the walls of the balloon 40.

The balloon 40 is generally formed from two sheets or panels of material, preferably defining anterior and posterior surfaces of the flat balloon 40. The panels 52 are fused or welded together around the periphery, creating a substantially fluid tight seam 56 that defines the inflatable space 58 in the balloon 40. Preferably, the seam 56 is heat sealed or sonic welded at the periphery as shown in FIG. 3A. Because the outer edges 54 of the peripheral seam 56 may be rough or sharp and may cause tissue trauma during use of the balloon, the seam 56 is preferably inverted or substantially contained within the inflatable space 58 in the balloon 40, as shown in FIG. 3B. This may be achieved by welding the periphery of the panels 52 to create a seam 56, turning the panels 52 inside out, and compressing the panels 52 together, thereby providing reentrant or partially reentrant outer edges 54 around the periphery of the balloon 40. The reentrant edges 54 around the periphery of the finished balloon 40 provide a substantially smooth profile that contacts the tissues atraumatically when the balloon 40 is inflated to develop the space. The balloon 40 may be fabricated in a manner such that part or all of the peripheral seam 56 is inverted. Alternatively, the peripheral trim 55 after welding or bonding may be extended beyond the weld periphery of the seam 56 to assure that the edges 54 will fold flat against the balloon surface 52 when in contact with tissue during inflation, as shown in FIG. 3D. In most instances, a margin of about 1 mm for the peripheral trim 55 should be adequate, but may vary with the balloon materials employed.

Figure 9:
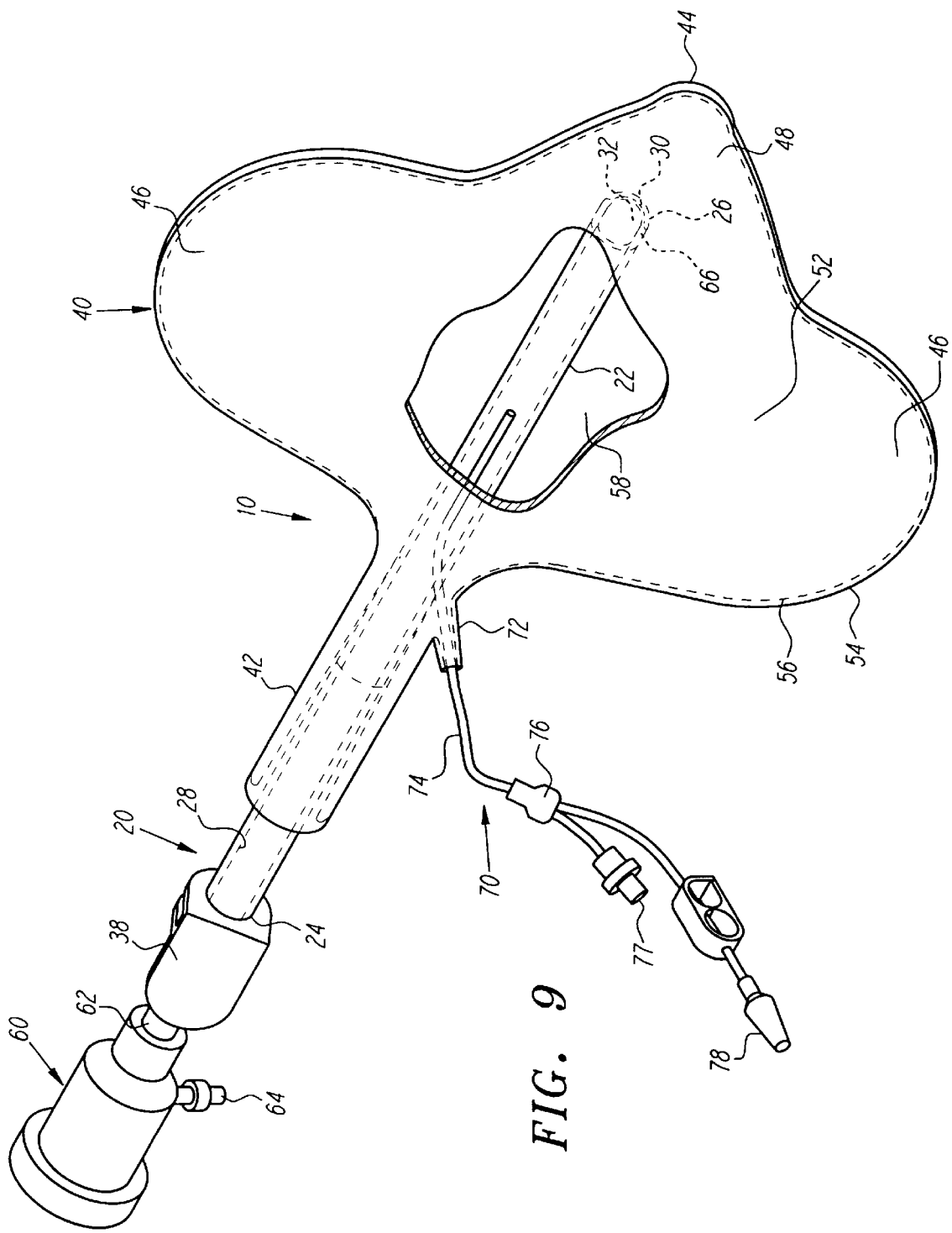
FIG. 9 is a perspective view of another preferred embodiment of a laparoscopic apparatus in accordance with the present invention, with the balloon uncovered and unrolled.

The balloon 40 is generally provided with a proximal sleeve or neck 42 into which the shaft 22 of the tunneling member 20 is inserted. As shown in FIG. 1, the neck 42 includes a handle 43 which includes a sealable bore (not shown) therethrough, although alternatively the neck 42 may be attached directly to the shaft 22, as shown in FIG. 9. The handle 43 may include an inflation port (not shown) in communication with the neck 42, allowing a suitable inflation medium, such as saline solution, to be introduced through the neck 42 into the inflatable space 58 of the balloon 40 for inflating the balloon 40.

Alternatively, as shown in FIG. 1, the balloon 40 may instead include an inflation lumen 70 in communication with the inflatable space 58 of the balloon 40. A flexible hollow tube 74 with an open distal end is inserted into an inflation lumen extension 72 on the balloon 40 and secured in a fluid tight manner thereto. The proximal end of the flexible tube 74 is secured to a conventional wye adapter 76 including an inflation fitting 77 and an evacuation fitting 78. Alternatively, in some instances, as with a tissue expander, the balloon may not include a proximal sleeve or handle (not shown), only a fill lumen and an injection port. The seam may then extend substantially entirely around the periphery of the balloon and may be provided inverted or with a margin as described above.

The inflation lumen 70 is generally provided as shown in FIG. 1 when the balloon edges 54 are not inverted at the point where the inflation lumen extension 72 is placed on the balloon 40. This configuration would be appropriate when none of the periphery of the balloon 40 is inverted, or when part of the periphery of the balloon 40 is welded (e.g. along the distal 48 and side portions 46), the welded portions are inverted, and the balance of the periphery of the balloon 40 (e.g. the portion including the inflation lumen extension 72) is then welded, the balance of the periphery thus remaining uninverted.

In embodiments where an entirely inverted periphery is desired, such as a tissue expander, the inflation lumen may be moved from the peripheral seam 56 of the balloon 40 onto one of the two balloon panels 52 from which the balloon 40 is formed (not shown). In such an embodiment, an adapter nipple 172 may be formed as shown in FIG. 3C. A flange 173 of the adapter nipple 172 is welded or bonded around a hole (not shown) formed in the desired balloon panel. After peripheral welding of the balloon seam, the balloon may be inverted through the nipple 172 and an inflation tube (not shown) may be bonded or welded to the neck 174 of the nipple 172 by any suitable means. The resulting balloon is totally enclosed with an attached inflation lumen and no protruding seam edges. Alternatively, when welding or bonding the adapter nipple 172 onto the balloon, the balloon may be inverted and partially inflated, the inflation thus resisting the pressure of the welding or bonding fixture. Using these methods, or variations of them, balloons may be provided of various shapes and construction with predetermined amounts of exposed and/or inverted seams.

In addition to the panels 52 defining the walls of the balloon 40, the balloon 40 may be selectively strengthened using one or more reinforcing panels of material similar to that used for the walls of the balloon 40. For example, as shown in FIG. 4, one or more additional panels 59 may be included in the distal portion 48 of the balloon 40 to enhance the puncture-resistance of the distal portion 48, that is, to substantially minimize the risk of stretching or tearing the balloon 40. Such reinforcing panels may be attached to the walls of the balloon 40 by conventional adhesives and/or may be welded to the balloon 40. For example, FIG. 5 shows reinforcing panels 59 being fused in the seam SG on the periphery of the balloon 40. Preferably, the panels 59 are also adhered to the inside surface of the adjacent panel 52 using welding or adhesives. If the balloon 40 is to be inverted, the reinforcing panels 59 may be fastened to the outside surface and then the balloon 40 may be inverted.

Figure 8:
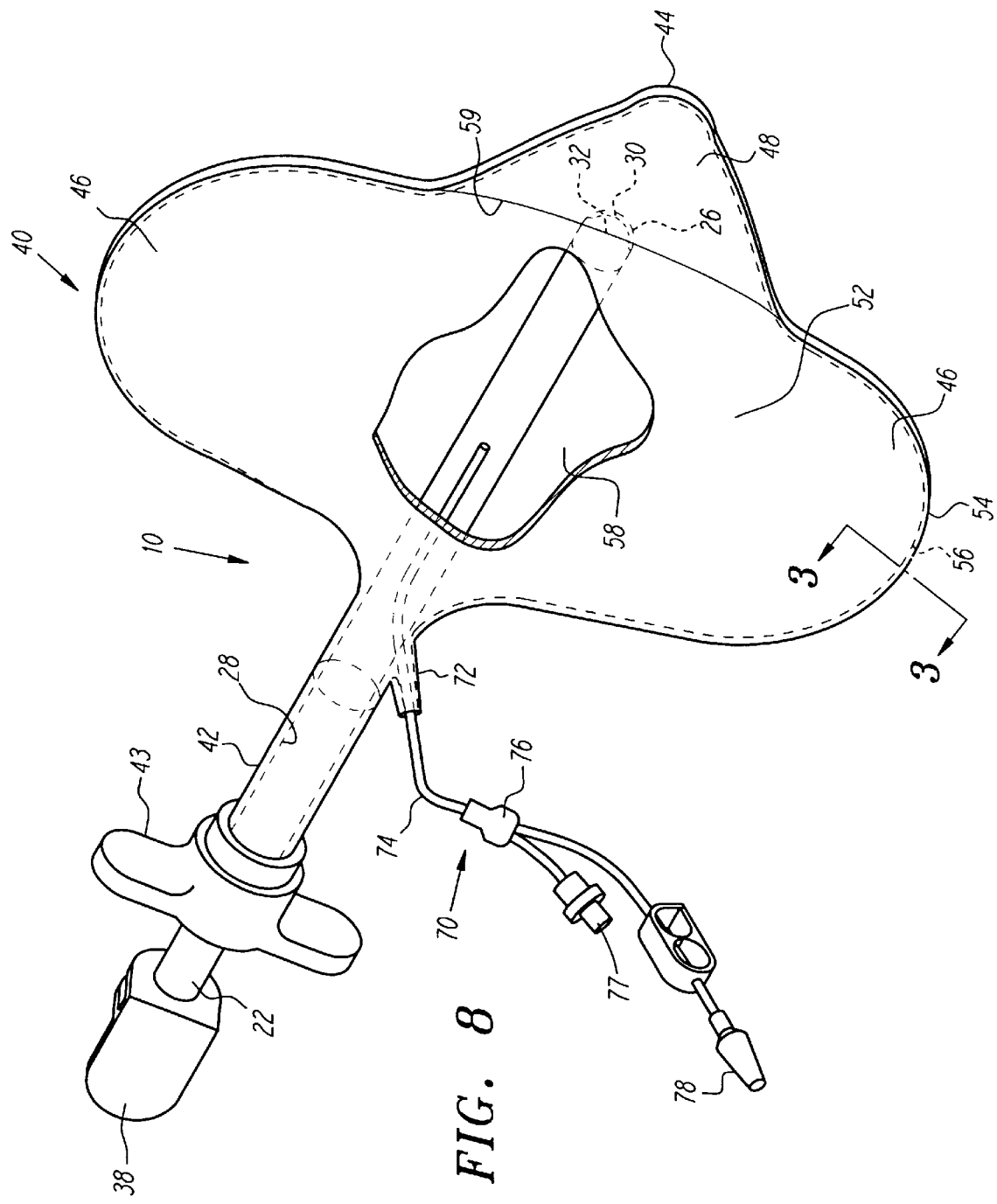
FIG. 8 is a perspective view of the embodiment of FIG. 1, prior to insertion of a laparoscope, with the balloon uncovered and unrolled.

Turning now to FIG. 8, when assembled into a complete apparatus 10, the obturator shaft 22 of the tunneling member 20 passes through the handle 43 and the neck 42 into the inflatable space 58 of the balloon 40. The distal end 26 of the shaft 22 extends through the balloon 40 to the distal portion 48 thereof, which may be reinforced as shown. Preferably, the distal end 26 does not extend into the distal portion 48, thereby allowing the distal portion 48 to be rolled, as described below. Alternatively, the distal end 26 may extend through the distal portion 48 until it presses against the nipple 44 in the balloon 40.

Preferably, the balloon 40 is wrapped and secured directly onto the obturator shaft 22 after the tunneling member 20 has been inserted into the balloon 40, allowing the balloon 40 to be fastened tightly thereto. The obturator shaft 22 is inserted into the flat balloon 40 until the distal end 26 reaches but does not enter the extension in the distal portion 48. The distal portion 48 of the balloon 40 is then rolled proximally along the anterior or top surface of the balloon 40, until the balloon 40 engages the distal end 26 of the tunneling member 20. Alternatively, the distal end 26 of the tunneling member 20 may be directed against the nipple 44 on the distal portion 48 of the balloon 40, whereupon the distal portion 48 is not rolled. The side portions 46 of the balloon 40 are then rolled laterally in, preferably along the posterior or bottom surface of the balloon 40, until the balloon 40 is substantially collapsed around the shaft 22 of the tunneling member 20.

The balloon 40 is then secured, preferably by an integral cover 80 that includes a weakened axial seam 82, as shown in FIG. 7. Alternatively, the balloon 40 may be covered with a removable sheath (not shown) that may be withdrawn proximally along the apparatus 10 after the apparatus is delivered to a desired location in a body. In either case, the cover substantially holds the balloon 40 until the time of deployment.

Turning to FIGS. 1, 6 and 7, a conventional laparoscope 60 is shown after it has been fully inserted into the apparatus 10. The laparoscope 60 includes a shaft 62 that is inserted into the bore in the handle 38 of the tunneling member 20, preferably until a distal end 66 of the laparoscope shaft 62 engages the lip 30 on the distal end 26 of the shaft 22, as shown in FIG. 6. The lip 30 thus prevents further advancement of the laparoscope shaft 62, and retains the distal end 66 of the laparoscope shaft 62 within the obturator shaft 22. The laparoscope 60 includes a fiber optic light port 64 to provide illumination to the lens (not shown) on the distal end 66 of the laparoscope shaft 62. Although an angled scope may be used, the improved lip 30 on the tunneling member 20 enhances the field of view axially through the distal end 26, allowing a straight scope to be used more effectively during tunneling, as described below.

The apparatus 10 may then be introduced into a body, for example, to create a preperitoneal space to permit laparoscopic hernia repair. An incision is made in the skin of a patient, and the distal 26 end of the tunneling member 20, covered by the rolled balloon 40, is introduced between desired tissue layers. The tunneling member 20 is advanced along with the rolled balloon 40 and the laparoscope 60 through the body to a desired location therein. Although the balloon 40 covers the opening 32 in the distal end of the tunneling member 20, its substantially transparent walls do not obstruct substantially light transmission or visualization therethrough. Thus, during tissue dissection from the advancement of the tunneling member, the laparoscope 60 allows continuous monitoring of the progress of the apparatus 10 to the desired location.

Once the tunneling member 20 reaches the desired location, preferably the desired preperitoneal location, the balloon 40 is deployed. Preferably, the balloon 40 is inflated, causing the weakened seam 82 on the cover 80 to tear, thereby exposing the balloon 40 within the space. Alternatively, if a sheath (not shown) is used, the sheath is withdrawn by pulling it proximally over the tunneling member 20 and out the incision. The balloon 40 is then inflated by introducing fluid, such as saline solution, through the inflation lumen 74 into the inflatable space 58 in the balloon 40. This causes the balloon 40 to expand, unrolling the rolled portions, causing tissue dissection and developing the anatomic space.

The method of preparing the collapsed balloon 40 described above is particularly useful in developing a preperitoneal space for laparoscopic hernia repair. Preferably, prior to inflating the balloon 40, the tunneling member 20 is oriented such that the anterior surface of the balloon 40 is directed towards the posterior side of the pubis. As the balloon 40 is inflated, the sides 46 unroll prior to the distal portion 48, thus substantially anchoring the balloon 40 within the space. Thereafter, as the distal portion 48 unrolls, it engages the posterior surface of the pubis space, clearing the distal field, and thus enabling improved observation of Cooper's ligament in the space being developed.

The unrolling action of the distal portion 48 is particularly useful for laparoscopic hernia procedures. First, if the tunneling member 20 is not inserted as deeply behind the pubis as desired, the distal portion 48 extends the space being developed distally. In addition, the unrolling of the distal portion along the posterior surface of the pubis enhances visualization of Cooper's ligament. Cooper's ligament, which has a substantially white appearance, is a particularly useful landmark structure located on the posterior surface of the pubis, thus improving a surgeon's orientation within the space.

Referring once again to FIGS. 3A and 3B, the improved outer edges 54 and seam 56 of the balloon 40 in accordance with the present invention also substantially enhance visualization during space development. When the balloon 40 is inflated, the sides 46 and the distal portion 48 of the balloon 40 unroll, moving the outer edges 54 along tissue surfaces of the space being developed. Because the peripheral seam 56 is inverted, the reentrant outer seam profile of the balloon 40 is substantially smooth and flexible in its contact with tissue and moves along the tissue surfaces with minimal scratching or tearing, minimizing bleeding. Particularly when the distal portion 48 is unrolled in the preperitoneal space, minimized bleeding is important for improving visualization.

Another important feature of the apparatus 10 in accordance with the present invention is the lip 30 on the tunneling member 20, and the recessed area 36 defined by the lip 30. Referring to FIGS. 2A and 2E, during tunneling dissection, the lip 30 provides a substantially rounded, blunt distal edge 34, that allows the distal end 26 of the tunneling member 20 to advance through body tissues with minimized tissue trauma. In addition, the blunt distal edge 34 substantially reduces the risk of puncturing or tearing the balloon 40 when the tunneling member 20 is advanced through the body and/or when the tunneling member 20 is moved during inflation of the balloon 40 to visualize the space being developed.

In addition, the lip 30 defines an open center area 36 in the opening 32 that substantially enhances the axial field of view through the distal end 26 of the tunneling member 20. This allows a straight scope to be used more effectively to view axially out the distal end 26 of the tunneling member 20.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A laparoscopic apparatus for creating an anatomical working space between tissue layers in a body, said apparatus comprising:
    a tunneling member comprising a substantially rigid shaft having open proximal and distal ends, and having a passage extending therethrough between said proximal and distal ends, said passage being adapted to receive a laparoscope therein, said distal end including a "U" shaped lip thereon adapted to retain the laparoscope from extending beyond said distal end, and to enhance a field of view axially through said distal end; and
    a balloon having an inflatable space and being capable of assuming collapsed and inflated conditions, said balloon having a proximal sleeve for receiving said distal end of said tunneling member therein.

2. The apparatus of claim 1, wherein said lip comprises a substantially blunt distal end on said tunneling member.

3. The apparatus of claim 1, wherein said lip extends radially inward from a perimeter of said distal end, said lip thereby defining a recessed area in an opening in said distal end, said recessed area being adapted to enhance said field of view axially through said distal end.

4. The apparatus of claim 1, wherein said lip comprises a rounded substantially blunt distal end of said tunneling member, said lip being adapted to substantially minimize tissue trauma when said tunneling member is advanced through tissues in the body.

5. The apparatus of claim 1, wherein said balloon comprises two panels substantially fused together along a seam thereby defining said inflatable space, said seam extending around a periphery of said panels and being set in from outer edges of said panels.

6. The apparatus of claim 5, wherein said seam comprises a heat seal.

7. The apparatus of claim 5, wherein said outer edges of said panels define unfused outer edges of said balloon.

8. The apparatus of claim 1, wherein said balloon comprises two panels substantially fused together along a seam thereby defining said inflatable space, said seam being at least partially inverted into said inflatable space, said seam thereby having at least a partially reentrant outer profile.

9. The apparatus of claim 1, wherein said balloon includes an extended distal portion, said distal portion being adapted to be rolled proximally along a surface of said balloon, thereby at least partially defining said collapsed condition.

10. The apparatus of claim 1, wherein said balloon includes a reinforcing panel on a portion of said balloon, said reinforcing panel comprising a substantially transparent, flexible material, said reinforcing panel being adapted to enhance a puncture-resistance characteristic of said portion.

11. The apparatus of claim 10, wherein said balloon includes a distal portion, said reinforcing panel extending proximally from an outer seam of said distal portion.

12. The apparatus of claim 11, wherein said reinforcing panel extends proximally along an inside surface of said distal portion.

13. The apparatus of claim 10, wherein said material of said reinforcing panel is of the same material as said balloon.

14. An inflatable balloon for creating an anatomical working space between tissue layers in a body, said balloon comprising:
    two panels substantially fused together along a seam extending substantially around a periphery of said panels thereby defining an inflatable space within said panels, said seam being inverted into said inflatable space, said balloon thereby having at least partially reentrant outer edges; and
    an inflation lumen communicating with said inflatable space for inflating and deflating said balloon between inflated and collapsed conditions.

15. The balloon of claim 14, wherein said seam is substantially entirely inverted and wherein said seam extends substantially entirely around a periphery of said balloon.

16. The balloon of claim 14, wherein said inflation lumen includes an inflation lumen extension integrally formed by said two panels when said two panels are substantially fused together, said seam being uninverted along said inflation lumen extension.

17. The balloon of claim 14, wherein said inflation lumen includes an adapter nipple substantially fused to one of said panels.

18. A laparoscopic apparatus for creating an anatomical working space between tissue layers in a body, said apparatus comprising:
    a tunneling member comprising a substantially rigid shaft having proximal and distal ends, and having a passage extending from said proximal end towards said distal end for receiving a laparoscope therein; and a balloon having an inflatable spare and capable of assuming collapsed and inflated conditions, said balloon being secured to said distal end of said tunneling member, said balloon comprising two panels substantially fused together along a seam extending at least partially around a periphery of said panels thereby defining said inflatable space within said panels, said seam being at least partially inverted into said inflatable space, said balloon thereby having nonoverlapping, at least partially reentrant outer edges.

19. The apparatus of claim 18, wherein said balloon is formed by a process comprising the steps of:

welding the periphery of the panels to create the seam;

turning the panels inside out; and compressing the panels together to create the at least partially reentrant outer edges.

20. The apparatus of claim 18, further comprising an inflation lumen communicating with said inflatable space for inflating said balloon from said collapsed condition to said inflated condition.

21. The apparatus of claim 18, wherein said balloon includes a proximal sleeve for receiving said distal end of said tunneling member therein.

22. A method for assembling an apparatus for use in developing an anatomic space at a desired location within a body, said method comprising the steps of:

providing a substantially rigid tunneling member having, open proximal and distal ends providing an inflatable balloon, the balloon having anterior and posterior surfaces, and having side portions and a distal portion;

rolling the distal portion of the inflatable balloon proximally along the anterior surface of the balloon;

rolling the side portions of the inflatable balloon laterally in along the posterior surface of the balloon subsequent to rolling the distal portion; and securing the balloon to the distal portion of the tunneling member.

23. The method of claim 22, comprising the additional step of inserting a laparoscope into the proximal end of the tunneling member.

24. The method of claim 22, wherein the balloon comprises a substantially transparent material.

25. The method of claim 22, wherein said securing the balloon step includes inserting the distal portion of the tunneling member into a proximal sleeve of the balloon.

26. A method for developing an anatomic space at a desired location within a body using a substantially rigid tunneling member having, an inflatable balloon thereon, the balloon having anterior and posterior surfaces, side portions and a distal portion, the distal portion being, provided in a proximally rolled condition along, the anterior surface and the side portions being provided in a laterally rolled in condition along the posterior surface, the method comprising the steps of:

advancing the tunneling member and rolled balloon through an incision to a desired location within the body;

orienting the tunneling member such that the anterior surface of the balloon is directed towards a tissue surface; and inflating the balloon to cause tissue dissection, the distal portion of the balloon unrolling as the balloon is inflated, thereby clearing the tissue surface as it unrolls and enhancing visualization thereof.

27. The method of claim 26, wherein the step of inflating the balloon comprises the steps of:

initially inflating the balloon, thereby unrolling the side portions of the balloon and anchoring the balloon at the desired location; and continuing balloon inflation, thereby unrolling the distal portion of the balloon.

28. The method of claim 26, comprising the additional step of inserting a laparoscope into the proximal end of the tunneling member.

29. The method of claim 26, wherein the balloon comprises substantially transparent material.

30. The method of claim 26, wherein said step of securing the balloon includes inserting the distal portion of the tunneling member into a proximal sleeve of the balloon.

* * * * *

UNITED STATES PATENT AND TRADEMARK OFFICE
CERTIFICATE OF CORRECTION

PATENT NO      :   6,015,421
DATED          :   January 18, 2000
INVENTOR(S)    :   JAN M. ECHEVERRY et al.

It is certified that error appears in the above-identified patent and that said Letters Patent are hereby corrected as shown below:

Column 5, line 32, please change "283" to -- 28 --.

Column 5, line 36, please change "20" to -- 22 --.

Column 5, line 39, please change "20" to -- 22 --.

Column 6, line 2, after "panels", please add -- 52 --.

Column 7, line 30, please change "SG" to -- 56 --.

Column 8, line 45, please change "lumen" to -- tube --.

Signed and Sealed this

Fifteenth Day of May, 2001

Attest:

NICHOLAS P. GODICI

Attesting Officer      Acting Director of the United States Patent and Trademark Office